United States Patent [19]

Reinehr et al.

[11] Patent Number: 5,478,935
[45] Date of Patent: Dec. 26, 1995

[54] PROCESS FOR THE PREPARATION OF HYDROXYPHENYL-1,3,5-TRIAZINES

[75] Inventors: Dieter Reinehr, Kandern, Germany; Jean P. Bacher, Buschwiller, France

[73] Assignee: Ciba-Geigy Corporation, Tarrytown, N.Y.

[21] Appl. No.: 321,492

[22] Filed: Oct. 12, 1994

[30] Foreign Application Priority Data

Oct. 15, 1993 [CH] Switzerland ............................ 3116/93

[51] Int. Cl.$^6$ .................................................. C07D 251/24
[52] U.S. Cl. ............................ 544/180; 544/216; 562/30
[58] Field of Search ...................................... 544/216, 180; 562/30

[56] References Cited

PUBLICATIONS

Reagents for Organic Synthesis, Fieser & Fieser, John Wiley and Sons, 1967 p. 1048.

(Khim. Geteritsikl. Soedin. (2), S. 350–353) (1969), C.A. 71 30455 k.

*Primary Examiner*—Yogendra N. Gupta
*Attorney, Agent, or Firm*—Kevin T. Mansfield

[57] ABSTRACT

A simple process for the preparation of a triazine of formula (1) is described, which comprises converting a dihydrotriazine of formula (2) with a reducing agent to a 1,3,5-triazine of formula (1).

The triazines obtained by the novel process are suitable UV absorbers for organic materials, in particular for polyester fiber materials, or suitable starting materials for the preparation of UV absorbers.

6 Claims, No Drawings

PROCESS FOR THE PREPARATION OF HYDROXYPHENYL-1,3,5-TRIAZINES

The present invention relates to a process for the preparation of hydroxyphenyl-substituted 1,3,5-triazines, to hydroxyphenyl-substituted dihydrotriazines and to a process for the preparation of said compounds, to the use of said dihydrotriazines as starting compounds for the preparation of UV absorbers as well as to the 1,3,5-triazines as UV absorbers.

The oxidation of dihydrotriazines to 1,3,5-triazines with chloranil and in good yield is described in Khim. Geteritsikl. Soedin. (2), p. 350–353 (1969). It is not possible to prepare homogeneous products with other oxidising agents. However, the use of chloranil as oxidising agent is very problematical for environmental reasons.

The object of the present invention is the preparation of 1,3,5-triazines, starting from dihydrotriazines, by another route.

Surprisingly, it has now been found that the oxidation of dihydrotriazines to the corresponding 1,3,5-triazines is achieved in simple manner and in good yield with certain compounds which are usually used as reducing agents.

Accordingly, the present invention relates to a process for the preparation of a triazine of formula

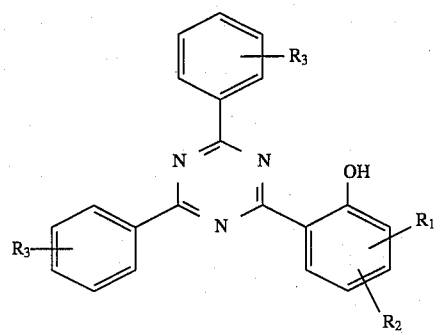

(1)

which comprises converting a dihydrotriazine of formula

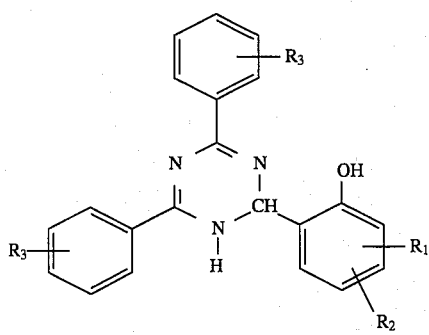

(2)

with a compound which is known as reducing agent to the compound of formula (1), wherein in formulae (1) and (2)

$R_1$, $R_2$ and $R_3$ are each independently of one another hydrogen, halogen, $C_1$–$C_{18}$alkyl, $C_1$–$C_{18}$alkoxy or —C≡N.

$C_1$–$C_{18}$Alkyl and $C_1$–$C_{18}$alkoxy are straight chain or branched alkyl or alkoxy radicals, typically methyl, ethyl, n-propyl, isopropyl, n-butyl, sec-butyl, tert-butyl, amyl, isoamyl or tert-amyl, heptyl, octyl, isooctyl, nonyl, undecyl, dodecyl, tetradecyl, pentadecyl, hexadecyl, heptadecyl or octadecyl, and, respectively, methoxy, ethoxy, propoxy, butoxy, pentoxy, hexoxy, heptyloxy, octyloxy, isooctyloxy, nonyloxy, undecyloxy, dodecyloxy, tetradecyloxy, pentadecyloxy, hexadecyloxy, heptadecyloxy or octadecyloxy.

Halogen is chloro, bromo or iodo. Chloro is preferred.

In the process of this invention the reducing agents used are typically dithionites, pyrosulfites, sulfites and thiosulfites. Sodium bisulfite or sodium dithionite are preferred.

The reaction may be carried out in the temperature range from 0°–150° C., preferably from 20°–80° C. The reaction time is usually from 1 to 20 hours, preferably from 2 to 8 hours.

The reaction is usually carded out in a polar solvent. Suitable solvents may be for example: dimethyl formamide (DMF), dimethyl acetamide, dimethyl sulfoxide, N-methyl pyrrolidone or sulfolane. The preferred solvents are DMF or a mixture of water and DMF, or dimethyl acetamide (DMA), or a mixture of dimethyl acetamide and water.

Dihydrotriazines suitable for the process of this invention are preferably those of formula (2), wherein $R_1$ is hydrogen, 4-OCH$_3$ or 3-OCH$_3$, and $R_2$ and $R_3$ are each independently of the other hydrogen or 4-OCH$_3$.

Some of the dihydrotriazines of formula (2) are described in Khim. Geteritsikl. Soedin. (2), p. 350–353 (1969), and some are novel compounds. These novel compounds are a further object of this invention. They correspond to formula

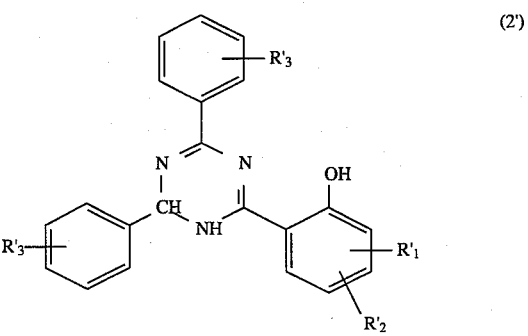

(2')

wherein $R'_1$, $R'_2$ and $R'_3$ are each independently of one another hydrogen, halogen, $C_1$–$C_{18}$alkyl, $C_1$–$C_{18}$alkoxy or —C≡N, with the proviso that $R'_1$, $R'_2$ and $R'_3$ are not simultaneously hydrogen.

The preparation of these novel dihydrotriazines is carded out in per se known manner by reacting 2 mol of a benzamidine hydrohalide of formula

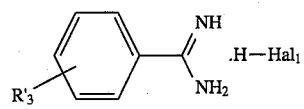

(3')

with 1 mol of a α-hydroxybenzaldehyde of formula

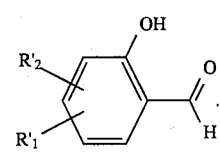

$R'_1$ and $R'_2$ are as defined in formula (2'), and Hal$_1$ is halogen.

The benzamidine hydrohalide may suitably be benzamidine hydrobromide and is preferably benzamidine hydrochloride.

The dihydrotriazines of formulae (2) and (2') are starting materials for the preparation of UV absorbers. The triazines of formula (1) are useful UV absorbers for organic materials, in particular for polyester fiber materials, and are distinguished by good properties.

The invention is illustrated by the following Examples in which percentages are by weight.

Preparation of the hydroxyphenyl-1,3,5-triazines

EXAMPLE 1

103 g (0.6 mol) of benzamidine hydrochloride (c. 91%) and 108 g (0.6 mol) of a 30% methanolic solution of sodium methylate are added to 100 ml of methanol. To the white suspension so obtained are added 65.1 g (0.3 mol) of 2-hydroxy-4-methoxy-benzaldehyde (69.4% solution in DMF) dropwise, and the colour then changes to ochre yellow. The suspension is heated to 38°–40° C. and stirred at this temperature for 16 hours. Subsequently the suspension is cooled to 10° C. and filtered. The filter product is washed first with 300 ml of methanol/water in the ratio of 1:1, then with 1.5 l of water and dried under vacuum at 110° C. to give an almost colourless product of formula

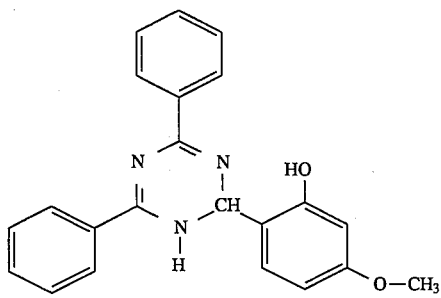
(101)

Yield: 72 g (67.2% of theory)
m.p.: 173°–174° C.

EXAMPLE 2

35.7 g (0.1 mol) of the product obtained in Example 1 are dissolved in 350 ml of dimethyl formamide (DMF). To this solution are added 38.3 ml of a 40% aqueous solution of sodium bisulfite over 30 minutes at 45° C. The solution is stirred for 6 hours at 48° C. and then diluted with 300 ml of water and filtered. The filter product is dried under vacuum at 110° C. to give the pale beige product of formula

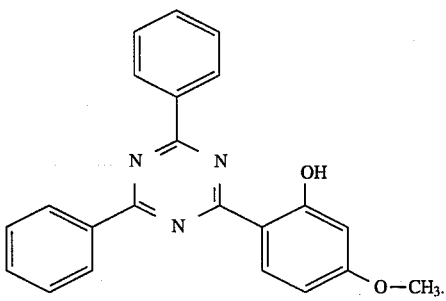
(102)

Yield: 32.5 g (91.5% of theory)
m.p.: 203° C.

EXAMPLE 3

The procedure of Example 2 is repeated, but using 350 ml of dimethyl acetamide instead of 350 ml of DMF, giving the compound of formula (102). Yield: 89% of theory.

EXAMPLE 4

The procedure of Example 1 is repeated, but using 0.3 mol of salicylaldehyde instead of 0.3 mol of 2-hydroxy-4-methoxy-benzaldehyde, giving the dihydrotriazine of formula

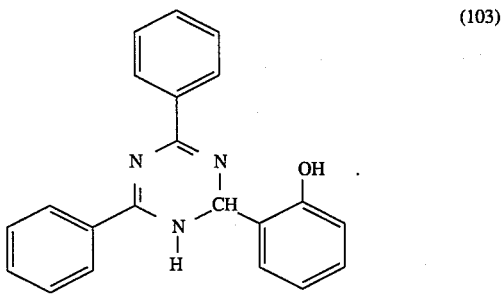
(103)

Yield: 94 g (96% of theory)
m.p.: 182° C.

EXAMPLE 5

The procedure of Example 2 is repeated, but using 32.3 g (0.098 mol) of the product obtained in Example 4. The reaction product of formula

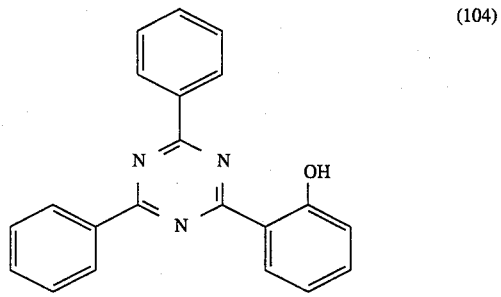
(104)

is obtained as a yellowish product.
Yield: 22 g (69% of theory)
m.p.: 246°–247° C.

EXAMPLE 6

The procedure of Example 5 is repeated, but using sodium dithionite instead of sodium bisulfite, giving the reaction product of formula (104). Yield: 65% of theory.

EXAMPLE 7 to 9

The following dihydrotriazines (Table 1) may be prepared in accordance with the general procedure of Example 1:

TABLE 1

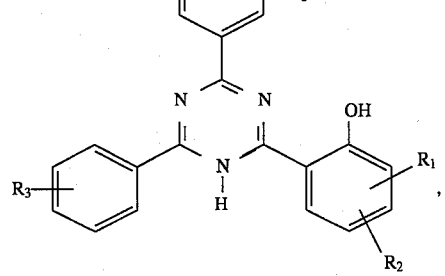

| Compound of formula | $R_1$ | $R_2$ | $R_3$ | Yield | m.p.[°C.] |
|---|---|---|---|---|---|
| (105) | H | $OCH_3$ | $OCH_3$ | 41% | 171 |
| (106) | $OCH_3$ | H | H | 87% | 197 |
| (107) | $OCH_3$ | H | $OCH_3$ | 82% | 205 |

EXAMPLES 10 to 12

In accordance with the general procedure of Example 2 the dihydrotriazines obtained in Examples 7 to 9 are converted into the corresponding triazines (Table 2)

TABLE 2

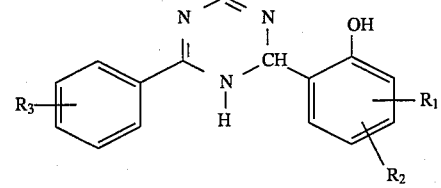

| Compound of formula | $R_1$ | $R_2$ | $R_3$ | m.p. [°C.] |
|---|---|---|---|---|
| (108) | H | $OCH_3$ | $OCH_3$ | 214 |
| (109) | $OCH_3$ | H | H | 214 |
| (110) | $OCH_3$ | H | $OCH_3$ | 198 |

What is claimed is:

1. A process for the preparation of a triazine of formula

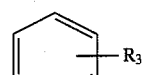

(1)

which comprises converting a dihydrotriazine of formula

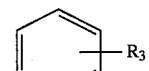

(2)

by reacting with a compound sodium dithionite or sodium bisulfite to the compound of formula (1), wherein in formulae (1) and (2)

$R_1$, $R_2$ and $R_3$ are each independently of one another hydrogen, halogen, $C_1$–$C_8$alkyl, $C_1$–$C_8$alkoxy or —C≡N.

2. A process according to claim 1, wherein the reaction is carried out in the temperature range from 0° to 150° C.

3. A process according to claim 1, wherein the reaction is carried out in a polar solvent or solvent mixture.

4. A process according to claim 3, wherein the solvent is selected from the group consisting of dimethyl formamide, dimethyl acetamide, dimethyl sulfoxide, N-methyl pyrrolidone and sulfolane.

5. A process according to claim 3, wherein the solvent is a mixture with water.

6. A process according to claim 1, wherein
$R_1$ is hydrogen, 4-$OCH_3$ or 3-$OCH_3$,
$R_2$ and $R_3$ are each independently of the other hydrogen or 4-$OCH_3$.

* * * * *